(12) United States Patent
Smith et al.

(10) Patent No.: US 9,770,252 B2
(45) Date of Patent: Sep. 26, 2017

(54) RETRIEVAL DEVICE AND RELATED METHODS OF USE

(71) Applicant: BOSTON SCIENTIFIC SCIMED, INC., Maple Grove, MN (US)

(72) Inventors: Paul Smith, Smithfield, RI (US); Samuel Raybin, Marlborough, MA (US); John Golden, Norton, MA (US); Daniel Lang, North Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 449 days.

(21) Appl. No.: 14/209,710

(22) Filed: Mar. 13, 2014

(65) Prior Publication Data

US 2014/0276910 A1 Sep. 18, 2014

Related U.S. Application Data

(60) Provisional application No. 61/784,469, filed on Mar. 14, 2013.

(51) Int. Cl.
*A61B 17/221* (2006.01)
*A61B 17/3205* (2006.01)
*A61B 18/14* (2006.01)
*A61B 18/00* (2006.01)
*A61B 17/00* (2006.01)

(52) U.S. Cl.
CPC ...... *A61B 17/221* (2013.01); *A61B 17/32056* (2013.01); *A61B 18/14* (2013.01); *A61B 2017/00358* (2013.01); *A61B 2017/00893* (2013.01); *A61B 2017/2212* (2013.01); *A61B 2017/2217* (2013.01); *A61B 2018/00267* (2013.01); *A61B 2018/00482* (2013.01); *A61B 2018/00595* (2013.01); *A61B 2018/141* (2013.01); *A61B 2218/002* (2013.01)

(58) Field of Classification Search
CPC . A61B 17/32056; A61B 17/221; A61B 17/26; A61B 2017/2212; A61B 2017/2217; A61B 2018/1407; A61B 2018/141
USPC .................................................. 606/113, 127
See application file for complete search history.

(56) References Cited

U.S. PATENT DOCUMENTS

| | | | |
|---|---|---|---|
| 5,207,686 A | | 5/1993 | Dolgin |
| 5,281,238 A | * | 1/1994 | Chin et al. .................... 606/148 |
| 5,980,534 A | * | 11/1999 | Gimpelson ............ A61B 17/42 606/119 |
| 6,090,129 A | * | 7/2000 | Ouchi .......................... 606/206 |
| 2009/0036899 A1 | | 2/2009 | Carlton et al. |

* cited by examiner

*Primary Examiner* — Diane Yabut
(74) *Attorney, Agent, or Firm* — Bookoff McAdrews, PLLC

(57) ABSTRACT

A medical device and a method for manipulating a tissue. The medical device includes two or more bars, a snare loop and a constricting element. Each bar includes a proximal end, and one or more distal ends, such that the bars are in close proximity at the proximal end. The snare loop maybe coupled to the distal ends of the bars. The constricting element maybe movably coupled to the bars, such that the constricting element expands the snare loop when positioned at the proximal end of the plurality of bars while the constricting element collapses the snare loop when positioned at the distal end of the plurality of bars, thus, keeping the distal end of the snare loop stationary with respect to the tissue.

20 Claims, 2 Drawing Sheets

RETRIEVAL DEVICE AND RELATED METHODS OF USE

CROSS-REFERENCE TO RELATED APPLICATIONS

This application claims the benefit of priority from U.S. Provisional Application No. 61/784,469, filed on Mar. 14, 2013, the entirety of which is incorporated by reference herein.

FIELD OF THE DISCLOSURE

Embodiments of the present disclosure relate generally to medical devices and procedures. Particularly, embodiments of the present disclosure relate to medical devices to perform tissue resection and/or retrieval during minimally invasive medical procedures.

BACKGROUND

Tissue resection procedures, such as polypectomy, are carried out by inserting introduction sheaths, such as endoscopes or laparoscopes, into the body of a patient through incisions or natural anatomical openings (e.g., oral, vaginal, and/or anal cavities). Traditionally, such devices employ snares, typically designed as loops, for performing tissue resection procedures. State of the art snares used for various tissue resection procedures have a tendency to slip off of tissue that is intended to be ensnared, often requiring repeated efforts to capture the tissue before the resection procedures can be successfully performed.

One factor affecting snare slippage is that the snare loop is typically drawn towards the snare shaft as the snare is closed, disrupting the distal snare tip, which often acts as an anchor relative to the tissue surface.

The present disclosure is directed to overcoming one or more of the issues described above and/or other shortcomings in the art.

SUMMARY

Embodiments of the present disclosure relate to medical devices for performing tissue-ensnaring procedures during, e.g., tissue resection from inside a patient's body.

In accordance with an aspect of the present disclosure, the medical device includes two or more bars, a snare loop and a constricting element. Each bar includes a proximal end, and one or more distal ends, such that the snare loop may be coupled to the distal ends of the bars. Further, the constricting element may be movably coupled to the bars, such that the constricting element expands the snare loop when positioned at the proximal end of the plurality of bars while the constricting element collapses the snare loop when positioned at the distal end of the plurality of bars, thus, keeping the distal end of the snare loop stationary with respect to the tissue.

In accordance with another aspect of the disclosure, a method for manipulating a tissue is described. The method includes introduction of the medical device into a body such that the distal end of the snare loop of the device is placed on the tissue. Thereafter, the snare loop is collapsed keeping the distal end of the snare loop stationary with respect to the tissue.

In accordance with the disclosure, another method for manipulating a tissue is described. The method includes introduction of the medical device into a body such that the distal end of the snare loop of the device is placed on the tissue. Thereafter, the snare loop is collapsed by moving a constricting element of the medical device distally, thus, keeping the distal end of the snare loop stationary with respect to the tissue.

In accordance with the disclosure, another method for manipulating a tissue is described. The method includes introduction of the medical device into a body such that the distal end of the snare loop of the device is placed on the tissue. Thereafter, the snare loop is collapsed by extending an actuation tube of the medical device distally, thus, keeping the distal end of the snare loop stationary with respect to the tissue while the tissue is manipulated.

Additional objects and advantages of the present disclosure will be set forth in part in the description which follows, and in part will be understood from the description, or may be learned by practice of the claimed invention.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and, together with the description, serve to explain the principles of the disclosure.

DESCRIPTION OF THE EMBODIMENTS

Reference will now be made in detail to embodiments of the present disclosure, examples of which are illustrated in the accompanying drawings. Wherever possible, the same reference numbers are used throughout the drawings to refer to the same or like parts. The term "distal" refers to the end farthest away from a user when introducing a device into a patient. The term "proximal" refers to the end closest to the user when placing the device into the patient.

Overview

Embodiments of the present disclosure relate to medical devices used to retrieve and/or sever unwanted tissue as well as other unwanted material, such as stones, within a patient's body. For example, embodiments of the disclosed device may facilitate removal of unwanted tissue, such as cancerous polyps or lesions, from within a patient's body, including tissue disposed, e.g., on the mucosal walls of the colon, esophagus, stomach, or duodenum. A physician may also desire to resect tissue in order to conduct a biopsy or other examination. For convenience, the medical devices discussed here are referred to as "retrieval devices," it being understood that such devices are equally useful for severing unwanted tissue.

In some embodiments, a retrieval device may include a plurality of bars, a snare loop, and a constricting element. Each bar includes a distal end and a proximal end. The distal end of the bars may be coupled to the snare loop while the proximal ends may be in close proximity to each other. The proximal ends of the bars may be enclosed in, or surrounded by, an elongate shaft. Further, the constricting element may be movably coupled to the bars such that when the constricting element is placed at the proximal end of the bars, the snare loop is in an expanded position and when the constricting element is placed at the distal end of the bars, the snare loop is in a collapsed position. The movement of the constricting element is controlled by an actuating element, such as, for example, a guidewire, a resilient mechanism like a spring, or other suitable mechanism. The actuating element may pass through the elongate shaft. In various embodiments, the constricting element may be cylindrical, rectangular, oval, elliptical, conical, and similar configurations.

In various embodiments of the disclosure, the operation of the retrieval device includes collapsing the snare loop such that the distal end of the snare loop remains stationary with respect to the targeted tissue, thereby enabling steady grip of the tissue.

Exemplary Embodiments

Figure 1:
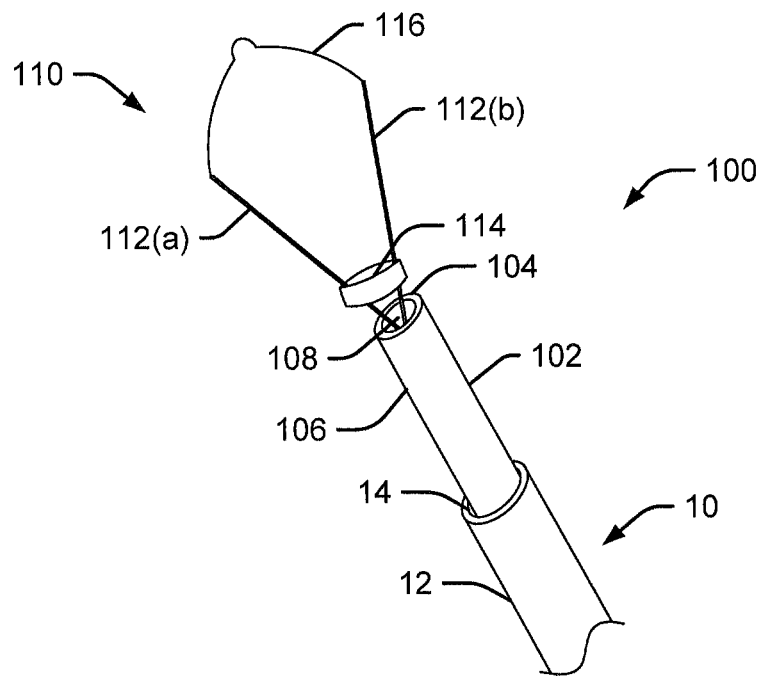
FIG. 1 is a schematic illustration of the perspective view of a distal portion of an exemplary retrieval device with expanded configuration of its snare loop.

FIG. 1 illustrates a perspective view of a distal portion of an exemplary retrieval device 100 depicting an expanded configuration of its snare loop, according to an embodiment of the present disclosure. The retrieval device 100 may be configured to be introduced into a patient's body through an incision or a suitable natural opening. In addition, the retrieval device 100 may be configured to be advanced to a desired location within a patient's body with the aid of a suitable introduction sheath, such as, e.g., an endoscope 10 that can further include a steerable elongate sheath 12 having a distal end 14, a proximal end (not shown) and one or more working channels extending therebetween.

As discussed above, endoscope 10 may include one or more working channels, wherethrough an operator may introduce one or more medical devices to extend out of the distal end 14 of elongate sheath 12. For example, during a resectomy procedure, an operator may introduce a suction device into one channel and another instrument, such as retrieval device 100, for example, into another channel. Additionally, from time to time during the procedure, the operator may insert a light source, a camera, an injector, or a morcellator within the one or more channels. The proximal end of the elongate sheath 12 may be connected to a hub assembly or handle (not shown) for operating the endoscope 10. The retrieval device 100 may include an elongate shaft 102 that further includes a proximal end (not shown), a distal end 104, and a lumen 106. The lumen 106 may be in communication with a distal opening 108 at the distal end 104 of the shaft 102, and the lumen 106 may extend through the entire length of the shaft 102. The elongate shaft 102 may be configured to be steerable independently of endoscope 10 using, e.g., a control wire or other similar mechanism. Further, the elongate shaft 102 may be coupled to the sheath 12 through its proximal end while supporting a medical device 110 at its distal end 104. The medical device 110 includes two or more bars 112(a), 112(b), one or more constricting elements 114, and a snare loop 116.

Figure 2:
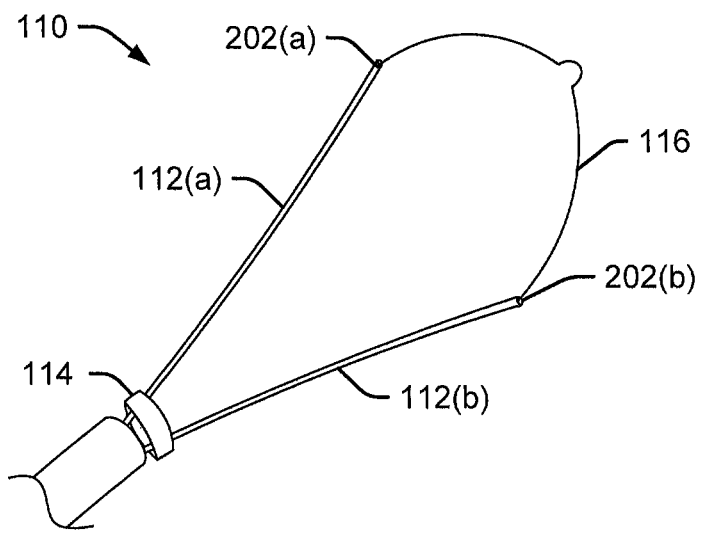
FIG. 2 is a schematic illustration of an exemplary snare apparatus of the retrieval device of FIG. 1 with the snare loop in an expanded configuration.

FIG. 2 illustrates an expanded configuration of the snare loop 116 of the medical device 110. The medical device 110 includes two or more bars 112(a) and 112(b), at least one constricting element 114, and the snare loop 116. Each bar 112(a) or 112(b) has a distal end 202(a) or 202(b) respectively, and a proximal end which may extend into the opening 108 of the distal end 104 of the shaft 102 (see FIG. 1). The bars 112(a) and 112(b) may be in close proximity to each other at their proximal ends while, towards their distal ends 202(a) and 202(b), the bars 112(a) and 112(b) may be farther apart and coupled to the snare loop 116. In an embodiment, the bars 112(a) and 112(b) along with the snare loop 116 may therefore form a V-shaped structure.

The snare loop 116 may be coupled to the bars 112(a) and 112(b) via a fixed connection like welding or may be detachably connected to the bars 112(a) and 112(b) via, for example, without limitation, a hook. The constricting element 114 may be movably coupled to the bars 112(a) and 112(b) such that the edges of the constricting element 114 slide on the bars 112(a) and 112(b) while the body of the constricting element 114 is placed in between the bars 112(a) and 112(b). In an embodiment, the distance between the two bars 112(a) and 112(b) towards the proximal end may be equal to the width of the constricting element 114. The constricting element 114 includes an actuating mechanism (shown in FIG. 3) that moves/slides the element 114 over the bars 112(a) and 112(b). In various embodiments, the actuation mechanism may include a guidewire, a spring mechanism or the like.

The bars 112(a) and 112(b) may be relatively rigid as compared to the snare loop 116. Alternatively, or in addition, the bars 112(a) and 112(b) may be supported by corresponding stiffening elements extending along with them. In an embodiment, the stiffening bars 112(a) and 112(b) may be hollow and may enclose the snare wire. Alternatively, the stiffening bars 112(a) and 112(b) may be solid. The wire used for the snare loop 116 and the bars 112(a) and 112(b) may be the same or different in structure and composition. For example, the snare loop 116 may be narrower and more rigid than the snare wire of the bars 112(a) and 112(b). The stiffening bars 112(a) and 112(b) could be manufactured from a variety of suitable biocompatible materials available to the art, such as nitinol, stainless steel, or polyimide. The chosen material may be based on desired stiffness, resilience, and other properties, as will be understood by those skilled in the art.

The snare wire may include a braided wire, multiple wires, or other suitable wires known to those skilled in the art. In addition, the material employed to manufacture such wires may include, but is not limited to, a rigid, a flexible, or a semi-rigid material. Exemplary materials may include metals, polymers, composites, alloys, or the like. The snare wire and/or the stiffening bars 112(a) and 112(b) may be coated with a suitable friction reducing material such as TEFLON®, polyetheretherketone, polyimide, nylon, polyethylene, or other lubricious polymer coatings, to reduce surface friction with the surrounding tissues. Alternatively, snare wire and/or the stiffening bars 112(a) and 112(b) may be made of, or covered with, an insulating layer, for example, a hydrophilic layer of polymers known in the art, to prevent inadvertent cauterizing of surrounding tissue.

In one embodiment, the snare loop 116 may be a wire configured to sever or retrieve unwanted tissue. Further, the snare loop 116 may be configured in a variety of shapes, such as a continuous loop, multiple loops, a basket, and the like. In one implementation, the snare loop 116 is substantially circular in shape, however, other configurations may include ellipsoids.

The constricting element 114 may slide over the bars 112(a) and 112(b) from the snare loop 116 to the proximal end of the bars 112(a) and 112(b). In various embodiments, the constricting element 114 may be cylindrical, oval, elliptical, rectangular, conical (similar configurations) in shape. Additionally, the constricting element 114 may include one or more holes through which an actuation element (for example, a guidewire) or snare wire may pass.

As shown in FIG. 2, the constricting element 114 when placed at the proximal end of the bars 112(a) and 112(b), may allow snare loop 116 to expand. For example, snare loop 116 may be configured to self expand and/or bars 112(a), 112(b) may be configured to self expand. The constricting element 114 may be arranged in a way such that a distally directed force on the constricting element 114 closes the snare loop 116 by drawing the distal end of the bars 202(a) and 202(b) towards each other. Distal forces may be applied on the constricting element 114 via the actuation element (shown in FIG. 3) coupled to the constricting element 114 which may be made of a conductive material, such as nitinol, stainless steel, and polyimide, to serve as an electrical path for cautery. In one embodiment, the distal ends of the bars 112(a) and 112(b) may include one or more features configured to act as a stop on movement of the constricting element 114 to prevent constricting element 114 to advance beyond a distal end of the bars 112(a) and 112(b).

A variety of mechanisms known in the art may be employed to selectively move/slide the constricting element 114 to expand or retract the snare loop 116. In one example, a push-pull mechanism, for example an actuation wire, may be employed as the actuation element for either manually or automatically expanding and/or retracting the snare loop 116. The movement of the constricting element 114 changes the area captured by the snare loop 116 without displacing/moving the snare loop with respect to the targeted tissue. In the expanded configuration, the snare loop 116 can be in a largest possible target acquisition area configuration based on the dimensions of the snare loop 116.

Figure 3:
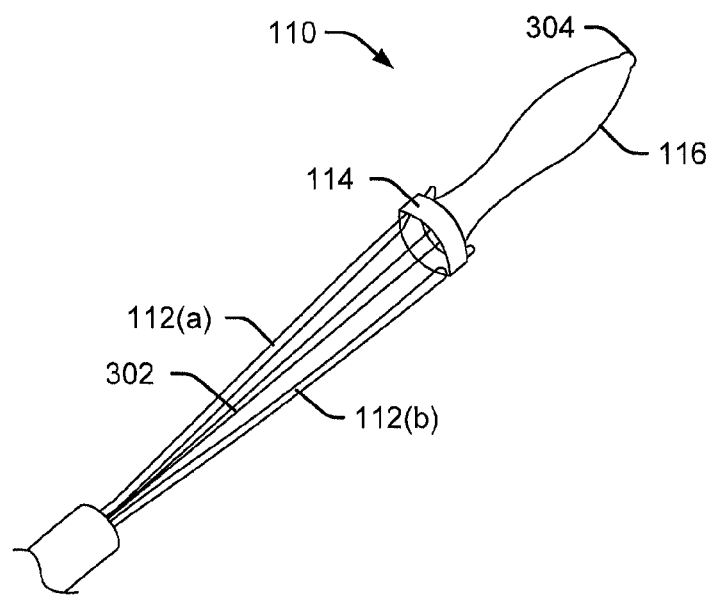
FIG. 3 is a schematic illustration of the retrieval device of FIG. 2 with the snare loop in a collapsed configuration.

FIG. 3 illustrates the collapsed configuration of the snare loop 116. In the collapsed configuration, the constricting element 114 is moved towards the distal end 202(a) and 202(b) of the bars 112(a) and 112(b) respectively, while snare 116 is held stationary relative to a tissue surface. The distal movement of the constricting element 114 forces the snare loop 116 to collapse as the ends of the snare loop 116 coupled to the bars 112(a) and 112(b) are brought in close proximity. The distal movement of the constricting element 114 may be facilitated by an actuation element 302. In the embodiment, the actuation element 302 is released to facilitate distal movement of the constricting element 114.

Optionally, a locking mechanism may be provided at the distal end 202(a) and 202(b) of the bars 112(a) and 112(b) respectively, to lock the constricting element 114, thereby reducing inadvertent movement of the constricting element 114 and enabling a steady grip of the tissue.

Now referring to the operation of the above embodiment, the device 110 is introduced into the body. While the device 110 is inserted, the snare loop 116 may remain in collapsed configuration with the constricting element 114 being placed at the distal end 202(a) and 202(b) of the bars 112(a) and 112(b) respectively. The movement of the inserted device 110 within the body is controlled till the snare loop 116 is placed on the targeted tissue. In an embodiment, the distal end 304 of the snare loop 116 is placed on the tissue after the device 110 is inserted into the body. The distal end 304 may, without limitation, include an outward projection in the loop 116 to help grip the tissue.

Thereafter, the snare loop 116 is expanded using the actuation element 302 coupled to the constricting element 114. When proximal forces are applied by the actuation element 302 to the constricting element 114, the element 114 moves towards the proximal end of the bars 112(a) and 112(b), thereby expanding the snare loop 116 to the desired area. In an embodiment, the snare loop 116 may be expanded to attain an area that fits the targeted tissue. The snare loop 116 and the bars 112(a), 112(b) remain stationary with respect to the tissue as the element 114 is moved proximally. It may be seen that the movement of the element 114 may only allow lateral movement of the snare 116 or the bars 112(a) and 112(b) while limiting any longitudinal movement of the snare 116 or the bars 112(a) and 112(b) with respect to the tissue. This enables the snare 116 to remain steady and address any slippage issues. The snare loop 116 may be adjusted such that it covers/surrounds the targeted tissue. Such adjustment may be achieved by the application of distal/proximal forces one or more times on the constricting element 114.

Once the snare 116 surrounds/covers the tissue, the tissue is manipulated. In an embodiment, the snare loop 116 may be configured for electrocauterization procedures to manipulate the tissue. Here, the snare loop 116 and/or constricting element 114 may be configured to conduct sufficient electric current to generate the heat required for electrocautery. In this embodiment, the snare loop 116 may also be substantially hollow with holes disposed on a surface (e.g., an internal surface) to provide, e.g., irrigation or lubrication during electrocauterization or any other medical procedure. Furthermore, the snare loop 116 can be configured to withstand repeated heat cycling without developing "hot spots" and breaking down. Further, the general characteristics of suitable materials and configurations of the snare loop 116 are known in the art to be able to select adequate materials and configurations for snare loop 116. In one embodiment, the snare loop 116 may be made of a suitable biocompatible material, e.g., stainless steel or nitinol.

After the tissue is manipulated, the constricting element 114 is moved towards the distal end 202(a) and 202(b) of the bars 112(a) and 112(b) respectively. The constricting element 114 moves on application of distal forces by the actuation element 302. Such forces may be applied by releasing the actation element 302 which in turn pushes the element 114 distally. The movement of the constricting element 114 from the proximal end to the distal end collapses the snare loop 116 as the distal ends 202(a) and 202(b) of the bars and the ends of the snare loop tied to the bars 112(a) and 112(b) come in close proximity to each other. It may thus be seen that the distal end 302 of the snare loop 116 remains stationary with respect to the tissue while the constricting element 114 is manipulated to expand/retract the snare loop 116. Even though the constricting element 114 is moved from the proximal end to the distal end or vice versa, the distal end 304 of the snare loop 116 and the device 110 remain in place without any longitudinal movement/displacement.

It may be apparent to a person skilled in the art that the teachings of the present disclosure as illustrated above are not limited to the above embodiment. In fact, the teachings of the present disclosure can be carried out using alternative embodiments such as described below as a second embodiment. In various embodiments, the actuation element may include without limitation, a guidewire, a spring mechanism, an actuation tube, a bracket, or a plate with one or more holes and the similar configurations.

Figure 4:
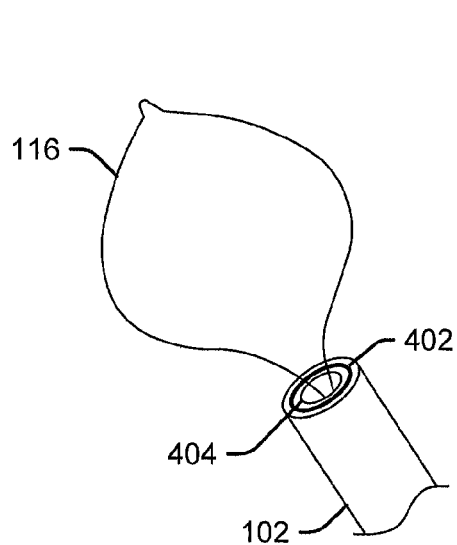
FIG. 4 is a schematic illustration of a second embodiment of an exemplary snare apparatus of the retrieval device of FIG. 1 with the snare loop in an expanded configuration.

FIG. 4 illustrates an expanded configuration of the snare loop 116 attached to the retrieval device 100 according to a second embodiment of the present disclosure. The distal end 104 of the elongate shaft 102 may include an actuation element in the lumen 106 of the shaft 102 and the actuation element may be capable of sliding within the shaft 102. In an embodiment, the actuation element includes without limitation, an actuation tube 402. The tube 402 may include a proximal portion (not shown) and a distal end 404. The tube 402 may extend from the shaft 102 such that it protrudes past the distal end 104 of the shaft 102 with the proximal end of the tube 402 enclosed/surrounded by the distal end 104 of the shaft 102. In one example, the proximal end of the tube 402 may be operatively attached to the shaft 102 using one or more sliders. The degree of flexibility of the tube 402 may be predetermined based on a variety of factors. Such factors include, but are not limited to, (1) the ability of the tube 402 to retract within the shaft 102, and/or (2) the amount of stiffness required to be imparted to the snare loop 116.

In addition, the tube 402 may include a lumen 406 (shown in FIG. 5) extending between the distal end 404 and the proximal end of the tube 402. Snare 116 may be disposed within the lumen 406. The tube 402 may be, e.g., a rigid cylindrical hollow bar configured to expand or collapse the snare loop 116 during use. In various embodiments, the length of the tube 402 may be such that it is less than, equal to or longer than the length of the shaft 102, depending upon the requirements of stiffness of the shaft 102. In an embodiment with the length of the tube 402 being less than the length of the shaft 102, the snare wire may be terminated on the inner side of the shaft 102. Alternatively, the snare wire may extend through the entire length of the lumen of the tube 402 and the shaft 102.

The tube 402 may further include a handle (not shown) that may slide the tube 402 in the lumen 106 of the shaft 102. An actuation wire of snare 116 (not shown in the figures) extends through the lumen 406 of the tube 402 and lumen 106 of the shaft 102.

As shown in FIG. 4, the snare loop 116 is completely expanded. To achieve this configuration of the snare 116, the tube 402 is completely retracted such that it is fully surrounded by the shaft 102. This results in the snare 116 being completely exposed and attain an expanded configuration. In an embodiment, the snare 116 may self-expand once the tube 402 is retracted in the absence of any controlling/manipulating forces.

The snare 116 may be made of such material that provides a required stiffness to the loop while it is in the expanded configuration and preferentially assumes a set shape when expanded, such as a circle or ellipse. The shaft 102 and the tube 402 can be made of the same or different types of materials, including those mentioned above, based on the degree of flexibility required for each of the them for accessing the targeted tissue. The shaft 102 and the tube 402 may be coated with a suitable friction reducing material such as TEFLON®, polyetheretherketone, polyimide, nylon, polyethylene, or other lubricious polymer coatings, to reduce surface friction with the surrounding tissues. The tube 402 may be made of, or covered with, an insulating layer, such as, for example, a hydrophilic layer of polymers known in the art, to prevent inadvertent cauterizing of surrounding tissue.

Further, the shaft 102, the tube 402, and the snare loop 116 may be coated with an antimicrobial covering to inhibit any microbial growth on its surface. For instance, the coating may include an anti-bacterial covering, which may contain an inorganic antibiotic agent, disposed in a polymeric matrix that adheres the antibiotic agent onto the surface of the snare loop 116. Furthermore, a drug-releasing coating may be applied to the surface of the snare loop 116 for assisting in delivery of drugs to the targeted tissue during operation.

Figure 5:
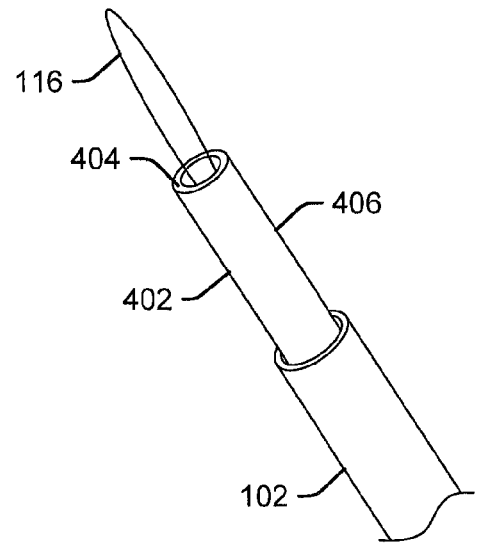
FIG. 5 is a schematic illustration of the retrieval device of FIG. 4 with the snare loop in a collapsed configuration.

FIG. 5 illustrates a collapsed view of the snare loop 116 according to the second embodiment of the present disclosure. In the collapsed configuration of the snare loop 116, the tube 402 is extended out of the shaft 102. This results in drawing/forcing the proximal ends of the snare 116 towards each other, with the tube 402 covering the snare loop 116 partially or completely. Though the snare loop 116 collapses, the distal end of the snare 116, shaft 102, and the snare wire (enclosed within the lumen of the shaft 102) remain in stationary with respect to the targeted tissue. The movement of the tube 402 may be controlled by the handle coupled to the tube 402. The wire of which the snare loop 116 is formed may be sufficiently flexible to retract the snare loop 116 in the collapsed position.

Referring to the operation of the second embodiment, when the retrieval device is inserted into the human body, the snare loop 116, in a collapsed configuration, may be placed on the tissue to be resected using a camera, and similar configurations. The distal end 304 of the snare loop 116 may include an outward projection to ensure that the snare loop is properly secured to the tissue. The tube 402 may be completely extended for the snare 116 to be in collapsed configuration. Thereafter, the snare loop may be expanded by moving the handle of the actuation tube 402 in the proximal direction to encompass or cover the desired tissue or area to be ensnared. The tissue may be manipulated by electrocautering, ablating, or other methods known in the art. The snare 116 may then be collapsed by extending the tube 402 from the shaft 102 such that the tube 402 partially or completely surrounds the snare 116. The tube 402 may be extended on application of distal forces on the handle that controls the movement of the tube 402.

By securing the distal end of the snare loop 116 onto the tissue or organ and adjusting the area of the snare loop required to hold the tissue using a movable actuation element, for example tube 402, the shaft 102 and the snare 116 are not required to be moved thereby eliminating the problem of snare loop slippage. The movement of the tube 402 distally/proximally results in manipulation of the snare 116 keeping the snare wire, the distal end of the snare loop 116, and the shaft 102 in place with respect to the targeted tissue.

It should be apparent that the retrieval device 100 of the present disclosure is useful to perform surgical, diagnostic, and therapeutic procedures in a wide variety of bodily locations. For example, removal of polyps detected during a routine colonoscopy could quickly be accomplished using the method discussed above. Additionally, stones or unwanted deposits can be engaged and removed from a variety of body lumens such as ureters, bladders, or the urethra. These and other procedures can be accomplished within the scope of the present disclosure.

Embodiments of the present disclosure may be used in any medical or non-medical procedure, including any medical procedure where appropriate resection of undesired body tissue is required. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

The invention claimed is:

1. A method for manipulating a tissue, the method comprising:
introducing a medical device into a body;
placing a distal end of a snare loop of the medical device on the tissue, wherein a first portion of the snare loop is coupled directly to a distal-most end of a first bar, and a second portion of the snare loop is coupled directly to a distal-most end of a second bar; and
collapsing the snare loop to a collapsed configuration, wherein the medical device includes a constricting element radially outward of the first and second bars, and a distance from a proximal end of the constricting element to a distal end of the constricting element is less than each of a distance from a proximal end of the first bar to a distal end of the first bar and a distance from a proximal end of the second bar to a distal end of the second bar,
wherein, in the collapsed configuration, the first portion of the snare loop is coupled directly to the distal-most end of the first bar, and the second portion of the snare loop is coupled directly to the distal-most end of the second bar.

2. The method of claim 1, wherein collapsing the snare loop comprises moving the constricting element of the medical device distally.

3. The method of claim 2, wherein collapsing the snare loop comprises releasing an actuation element facilitating distal movement of the constricting element.

4. The method of claim 2, further comprising expanding the snare loop by moving the constricting element proximally.

5. The method of claim 4, wherein expanding the snare loop comprises pulling an actuation element facilitating proximal movement of the constricting element.

6. The method of claim 1, further comprising electrocauterizing the tissue.

7. The method of claim 1, further comprising ablating the tissue.

8. The method of claim 1, wherein the first portion of the snare loop is a proximalmost end of the snare loop.

9. A medical device for manipulating a tissue, the medical device comprising:
a plurality of bars, wherein each bar comprises a proximal end and at least one distal end;
a snare loop coupled to a distal-most end of each of the distal ends of the plurality of bars, wherein the snare loop is more flexible than the plurality of bars; and
at least one constricting element movably coupled to the plurality of bars, wherein the constricting element allows the snare loop to expand when the constricting element is positioned at the proximal ends of the plurality of bars, wherein the constricting element collapses the snare loop when positioned at the distal ends of the plurality of bars, and wherein when the constricting element moves from the proximal ends of the plurality of bars to the distal ends of the plurality of bars, the plurality of bars move radially inward, and when the constricting element is positioned at the distal ends of the plurality of bars, at least a portion of the plurality of bars, proximal to the constricting element is uncovered by the constricting element, and, when the snare loop is collapsed, the snare loop remains coupled directly to the distal-most ends of the plurality of bars.

10. The medical device of claim 9, wherein the plurality of bars are substantially straight.

11. The medical device of claim 9, further including a plurality of stiffening elements coupled to the plurality of bars.

12. The medical device of claim 9 further including an actuation element coupled to the constricting element.

13. The medical device of claim 12, wherein the actuation element comprises one of a guidewire or a spring mechanism.

14. The medical device of claim 9, wherein the snare loop is an electrocautery snare loop.

15. The medical device of claim 9, wherein the constricting element is a ring, wherein a distance from a proximal end of the constricting element to a distal end of the constricting element is less than each of a distance from a proximal end of the first bar to a distal end of the first bar and a distance from a proximal end of the second bar to a distal end of the second bar.

16. The medical device of claim 9, wherein the plurality of bars includes a stop mechanism to limit distal movement of the constricting element.

17. The medical device of claim 16, wherein the stop mechanism is located at the distal end of at least one of the plurality of bars.

18. A method for manipulating a tissue, the method comprising:
introducing a medical device into a body;
placing a distal end of a snare loop of the medical device on the tissue; and
collapsing the snare loop by moving a constricting element of the medical device distally, wherein the constricting element is positioned radially outward of a plurality of bars, wherein the distal movement of the constricting element is stopped by a stop mechanism disposed on a distal end of at least one of the plurality of bars, and wherein each of the plurality of bars is tubular-shaped and defines a central lumen, and the snare loop extends through the central lumen of each of the plurality of bars.

19. The method of claim 18, further comprising expanding the snare loop by moving the constricting element proximally along the plurality of bars.

20. The method of claim 18, further comprising collapsing the snare loop by moving the constricting element distally along the plurality of bars.

* * * * *